United States Patent [19]
Danziger

[11] Patent Number: 5,948,771
[45] Date of Patent: Sep. 7, 1999

[54] METHOD FOR TREATING HEART FAILURE USING TETRAPYRROLES AND METALLOTETRAPYRROLES

[75] Inventor: Robert S. Danziger, New York, N.Y.

[73] Assignee: The Trustees of Columbia University in the City of New York, New York, N.Y.

[21] Appl. No.: 08/660,609

[22] Filed: Jun. 6, 1996

Related U.S. Application Data

[60] Provisional application No. 60/010,908, Jan. 31, 1996.

[51] Int. Cl.$^6$ ..................... A61K 31/555; C07D 487/22
[52] U.S. Cl. ............................................. 514/185; 540/145
[58] Field of Search .............................. 514/185; 540/145

[56] References Cited

U.S. PATENT DOCUMENTS

| | | | |
|---|---|---|---|
| 4,829,984 | 5/1989 | Gordon | 600/12 |
| 4,997,639 | 3/1991 | Aizawa et al. | 514/8 |
| 5,214,036 | 5/1993 | Beth et al. | 514/185 |
| 5,298,018 | 3/1994 | Narisco, Jr. et al. | 604/21 |
| 5,422,362 | 6/1995 | Vincent et al. | 514/410 |
| 5,447,939 | 9/1995 | Glasky et al. | 514/318 |
| 5,451,599 | 9/1995 | Graczyk et al. | 514/410 |

FOREIGN PATENT DOCUMENTS

91/16053   10/1991   WIPO .

OTHER PUBLICATIONS

Garthwaite, J. (1995) "Potent and Selective Inhibiton of Nitric Oxide–Sensitive Guanylyl Cyclase by 1H–[1,2,4] Oxadiazolo [4,3–a] quinoxalin–1–one" Molecular Pharmacology 48: 184–88.

Anderson, K.E. (1986) "Disposition of tin–protoporphyrin and suppression of hyperbilirubinemia in humans" Clin. Pharmacol. Ther. 39(5): 510–520.

Atanassova, et al. (1992) "Effects of Isosorbide–5–mononitrate and Isosorbide–2–mononitrat on the Contractile and Cyclie Nucleotides in Isoalted Heart Muscles of the Guinea–pig and Dog" J. Pharm. Pharmacol. 44(8): 663–666.

Balligand, et al. (1993) "Abnormal Contractile Funtion due to Induction of Nitric Oxide Synthesis in Rat Cardiac Myocytes Follows Exposure to Activated Macophage–conditioned Medium" Journal of Clinical Investigation 91(5): 2314–2319.

Balligand, et al. (1993) "Control of Cardiac Muscle Cell Function by an Endogenous Nitric Oxide Signaling System" Proc. Natl. Acad. Sci. 90(1): 347–51.

Berglund, et al. (1988) "Sn–Protoporphyrin Lowers Serum Bilirubin Levels, Decreases Biliary Bilirubin Output, Enhances Biliary Heme Excretion and Potently Inhibits Hepatic Heme Oxygenase Activity in Normal Human Subjects" Hepatology 8(3): 625–631.

Braughler, J.M. et al. (1979) "Purification of soluble guanylate cyclase from rat liver" Proc. Natl. Acad. Sci. (76) 1: 219–222.

Chen, L. et al. (1992) "Electron spin resonance determination and superoxide dismutase activity in polymorphonuclear leukocytes in congestive heart failure" Canadian J. Cardiol. 8(7): 756–60.

Ewing, J.F., (1994) "Induction of Heart Heme Oxygenase–1 (HSP32) by Hyperthemia: Possible Role in Stress–Mediated Elevation of Cyclic 3', 5'–Guanosine Monophosphate".

Gennaro, A.R., Ed., (1985) "Remington's Pharmaceutical Sciences", 17th ed., Mack Publishing Company, Easton, PA, p. 1418.

Greene, T.W., et al., 2nd Ed., (1981) Protective Groups in Organic Synthesis, John Wile and Sons.

Gross, E. et al. (1981) The Peptides–Analysis, Synthesis, Biology, Academic Press.

Habib, F., (1994) "Enhanced basal nitric oxide production in heart failure: another failed counter–regulatory vasodilator mechanism" Lancet 344(8919): 371–3.

Honeybourne, et al. (1979) "The Interaction of Mitochondrial Ferrochelatase with a range of Porphyrin Substrates" FEBS Letters 98(1): 207–210.

Ignarro, L.J., (1994) "Regulation of Cytosolic Guanylyl Cyclase by Porphyrins and Metalloporphyrins" Advances in Pharmacology 26:35–65.

Jones M.S. (1969) "The Structural Organization of Haem Synthesis in Rat Liver Mitochondria" The Biochemical Journal 113: 507–514.

Kappas, et al., (1988) "Sn–Protoporphyrin Use in the Management of Hyperbilirubinemia in Term Newborns With Direct Coombs–Positive ABO Incompatibility" Pediatrics 81(4): 485–497.

Lincoln, et al., (1991) "Towards an Understanding of the Mechanism of Action of Cyclic AMP and Cyclic GMP in Smooth Muscle Relaxation" Blood Vessels, 28: 129–137.

O'Murchu, B. et al. (1994) "Increased Production of Nitric Oxide in Coronary Arteries during Congestive Heart Failure" J. Clin. Invest. 93(1): 165–171.

Roberts, D.C. et al. (1983) "Unusual Amino Acids in Peptid Synthesis" The Peptides–Analysis, Synthesis, Biology Volume 5: 342–429.

Rubaltelli, F.F., (1989) "Tin–Protoporphyrin in the Management of Children with Crigler–Najjar Disease" Pediatrics 84(4): 729–31.

Schmidt, H.W. et al., (1991) "Purification on a soluble isoform of guanylyl cyclase–activating–factor synthase" Proc. Natl. Acad. Sci. USA, 88: 365–369.

(List continued on next page.)

*Primary Examiner*—Ceila Chang
*Attorney, Agent, or Firm*—John P. White; Cooper & Dunham LLP

[57] ABSTRACT

A method to improve the contractile function of the heart in myocarditis and other forms of heart failure is disclosed. The method consists essentially of administering a tetrapyrrole or metallotetrapyrrole which inhibits or reduces the endogenous guanylyl cyclase activity in cardiac myocyte of the patient.

11 Claims, 4 Drawing Sheets

OTHER PUBLICATIONS

Schmidt, H.W. et al., (1992) "NO, CO and OH Endogenous soluble guanylyl cyclase–activating factors" FEBS 307(1): 102–07.

Singh, N., et al. (1995) "Oxidative stress and heart failure" Mol. Cell. Biochem. 147: 77–81.

Slungaard, A.J. (1991) "Bromide–dependent Toxicity of Eosinophil Peroxidase for Endothelim and Isolated Working Rat Hearts: A model for Eosinophilic Endocaritis" Exper. Med. 173(1): 117–26.

Winlaw, D.A. et al. (1994) "Increased nitric oxide production in heart failure" Lancet 344 (8919): 373–4.

Wong, et al. (1992) "Receptor Gyanylyl Cyclases" J. Clin. Invest. 90(2): 299–305.

Yang, X. et al. (1994) "Induction of Myocardial Nitric Oxide Synthese by Cardiac Allograft Rejection" J. Clin. Invest. 94(2): 713–21.

Torfgard et al. "Mechanism of action of nitrates" Index Medicus 95:178406, 1995.

Fitton et al. "Isradipine. A review of its pharmacodynamic and pharmacokinetics properties and therapeutic use in cardiovascualr disease" Index Medicus 90:360912, 1990.

Colucci et al. "Mechanisms and implications of vasodilator tolerance in the treatment of congestive heart failure" Index Medicus 81:229559, 1981.

Stephenson et al. "Acetylcholinesterase inhibitors . . . ," CA 112:229664, 1990.

Silveira et al. "Vascular effects of acetylcholinesterase inhibitors . . . , " CA 117:103972, 1992.

Brunner et al. "Novel guanylyl cyclase inhibitor . . .. " CA 124:313545, 1996.

Luo et al. "Mettalloporphyrins inhibit oxide . . . " Eur. J. Pharm. mol. pharm. v.267, pp. 263–267, 1994.

Sulakhe et al. Biochem. J. v.157, pp. 705–712, 1976.

Wyngaarden et al. "Cecil textbook of medicine" Sander Co. pp. 107–108, 243–244, 1983.

METHOD FOR TREATING HEART FAILURE USING TETRAPYRROLES AND METALLOTETRAPYRROLES

This application claims the benefit of U.S. Provisional Application No. 60/010,908, filed Jan. 31, 1996, the content of which is incorporated by reference in this application.

BACKGROUND OF THE INVENTION

Heart or cardiac failure is defined as the pathological "state in which an abnormality of cardiac function is responsible for failure of the heart to pump blood at a rate commensurate with the requirements of the metabolizing tissues . . . and is frequently caused by a defect (decrease) in myocardial contraction." (Hurst, Willis J. (ed) 1990 *The Heart*, McGraw Hill Inc., New York, 388–440).

Heart failure is characterized by decreased cardiac contractility, i.e., inotropy. The causes are well known in the art. The mechanism is generally considered to be a reduction in the the force of contraction and may be directly attributed to a decreased contractile response of cardiac myocytes. Changes in cardiac myocytes from failing hearts include: increased oxygen consumption, decreased mitochondrial mass, oxidative phosphorylation, reduced intracellular calcium, sarcomere "overstretching", decreased myosin and myofibrillar ATPase activity, changes in myosin isoforms, and reduced $\alpha,\beta$-adrenoreceptors and $\alpha,\beta$-adrenergic signalling (Braunwald, E., *Textbook of Cardiovascular Disease*, W. B. Saunders Co., Philadelphia, Pa. (1994)).

Approaches to the treatment of heart failure have included: reducing the workload of the heart, reducing salt intake, diuretics, inotropic agents such as digitalis, and vasodilators.

Other approaches for primary treatment of reduced contractility in heart failure include drugs which: inhibit Na/K ATPase, such as digitalis glycosides; stimulate cAMP accumulation, such as $\beta$-adrenergic agonists and phosphodiesterase inhibitors; and increase myofilament sensitivity to calcium. In myocarditis, steroids and antibiotics have been used (Braunwald, E., *Textbook of Cardiovascular Disease*, 1990). The primary drawbacks of these methods has been lack of insufficient inotropic response, toxic effects during prolonged use, and loss of efficacy over time. Studies have shown that in spite of such primary treatments heart failure often persists with progression to death or, when possible, cardiac transplantation.

Even though various methods have been developed to treat heart failure, no single method has been found to be universally applicable and have a high therapeutic success rate. Heart failure remains one of the leading causes of death in the United States. Accordingly, there is a need to develop more efficacious therapies for the treatment of heart failure.

Recently, evidence that increases in myocyte cyclic guanosine-3',5'-monophosphate (cGMP) content concentration may contribute to reduced contractility in certain forms of heart failure has come to light. cGMP, a secondary messenger, has been shown to reduce the contractility of the heart and isolated cardiac myocytes (Atanassova, et al., (1995) J. Pharm. 44:663–666; Ballingand et al., (1993), Journal of Clinical Investigation 91(5):2314–2319; Balligand et al., (1993) PNAS 90(1)347–51). cGMP activates cGMP-dependent protein kinase (PkG). This leads to: 1) decrease in myofilament sensitivity to calcium via phosphorylation of troponin; and 2) reduction in intracellular calcium due to activation of sarcolemmal $Ca^{2+}$-ATPase and inhibition of voltage-dependent calcium channels by phosphorylations (Lincoln, T. M., and Cornwell, T. L., (1991) Blood Vessels 28:129–137).

The intracellular concentration of cGMP is regulated by cGMP-forming enzymes, i.e., guanylyl cyclases, and CGMP-degrading enzymes, i.e., CGMP phosphodiesterases. Soluble guanylyl cyclase, a cytosolic enzyme, which catalyzes the formation of cGMP from GTP, is an obligate heterodimer ($\alpha/\beta$) with an associated heme group (Wong, S. K. -F. and Garbers, D. L., (1992) J. Clin. Invest. 90:299–305; Baughler, J. M., et al. (1979) Proc. Natl. Acad. Sci. 76:219–222). Soluble guanylyl cyclase is activated by a variety of endogenously formed agonists, i.e., nitric oxide (NO), carbon monoxide (CO), hydroxyl radicals (OH), and possibly hydrogen peroxide ($H_2O_2$) (Schmidt, H. H. H. W., et al., (1991). Proc.Natl.Acad.Sci. USA, 88: 365–369; Schmidt, H. H. H. W., (1992) FEBS 307(1): 102–107).

Recent reports suggest that these endogenously formed activators are increased in various forms of heart failure, especially but not confined to those associated with inflammation (myocarditis and acute rejection associated with transplantation). Enhanced basal NO production has been reported both in human heart failure (Calver, A., (1994) Lancet 344(8919):371–3; Winlaw, D. S. et al., (1994) Lancet 344(8919):373–4) and animal models (Yang, X. et al., J. Clin. Invest. 94(2):714–21; O'Murchu, B. et al., (1994) J. Clin. Invest. 93(1):165–71). Increased production of oxygen free radicals by polymorphonuclear leukocytes, which infiltrate the myocardium, has been described in humans with congestive heart failure (Chen, L. et al., (1992) Canadian J. Cardiol. 8(7):756–60; Slungaard, A., (1991) J. Exper. Med. 173(1):117–26, line 13, p. 3). Increased oxidant stress, i.e., formation of $H_2O_2$ and oxygen free radicals has been detected in both inflammatory and dilated cardiomyopathies (Singh, N. et al., (1995) Mol.Cell.Biochem. 147:77–81). Heme oxygenase, an enzyme which forms CO from heme, has been shown to be induced in myocarditis (Ewing, J. F., (1994) J.Pharm.Exp.Ther. 271(1):408–14).

Selective inhibition or activation of enzyme pathways involved in the metabolism or catabolism of pharmacologically active compounds, such as cGMP, is well accepted in the pharmaceutical therapy of diseases. For the effective treatment of any given disease, targeting of the appropriate pathway(s) is key. The effect that modifying the activity of a given enzymatic pathway will have upon the disease in tissue or upon a subject receiving an enzyme activity modifier is unpredictable.

Glasky et al. (U.S. Pat. No. 5,447,939) recently discovered that guanylyl cyclase modifiers could be used to treat neurological disorders. The patent claims a method for treating neurological disorders by administering "a carbon monoxide dependent guanylyl cyclase modulating purine derivative." The disorders claimed are epilepsy, seizures, peripheral neuropathy, learning disability, cerebral palsy, psychiatric disorder, memory disorder and Huntington's disease.

Tetrapyrroles, in particular porphyrins and related compounds, have several known uses. Aizawa et al. (U.S. Pat. No. 4,997,639) discloses and claims a method for detecting cholesterol deposited in a mammal. The method involves administering a porphyrin carboxylic acid to the mammal, exposing the mammal to a light source and observing the fluorescence emitted from an area in which cholesterol is deposited.

R. T. Gordon (U.S. Pat. No. 4,829,984) discloses and claims a method for improvement of transplanting organs and preserving tissues. The method involves introducing particles (made from tetrapyrroles and metallotetrapyrroles) to the tissue, allowing time for intracellular accumulation of the particles, subjecting the tissue to a pulsing electromagnetic field, and allowing time to destroy cells mediating an immunological response.

Administration of tetrapyrroles has been found to be an effective treatment for several diseases. H. L. Narisco (U.S. Pat. No. 5,298,018) discloses and claims photodynamic therapy as a method for the treatment of cardiovascular disease, specifically atherosclerosis, by, first, administration of a photosensitizing agent, such as a porphyrin, to a mammal and, second, exposing of the mammal to a light source.

Vincent et al. (U.S. Pat. No. 5,422,362) discloses and claims a method of inhibiting restenosis. The method involves administering to a subject a "green" porphyrin without having to expose the subject to a light source.

In normal subjects, Sn-protoporphyrin IX has only been reported to lower serum bilirubin levels, decrease biliary bilirubin output, and enhance biliary heme excretion (Berlund, et al., (1988) Hepatology 8(3), 625–631). Sn-protoporphyrin has been used in the treatment of various rare diseases, i.e., Crigler-Najjar Disease (Rubaltelli, F. F., (1989) Pediatrics 84(4):728–731) and Gilbert's syndrome (Anderson, K. E., (1986) CLin.Pharmacol.Ther. 39:510–20), and has, therefore, been already approved for humans. As a result, it is believed to be relatively safe and the risk/benefit in severe heart failure acceptable.

Recent evidence suggests that porphyrins, particularly metalloporphyrins, interact at a common binding site on guanylyl cyclase. Some porphyrins and metalloporphyrins inhibit (Sn-protoporphyrin IX, Zinc-protoporphyrin IX, Manganese-protoporphyrin IX, N-Phenylprotoporphyrin IX, Deuteroporphyrin IX dimethyl ester, Hematoporphyrin IX dimethyl ester, Deuteroporphyrin IX disulfonate, Deuteroporphyrin IX bisglycol, and Coproporphyrin I) while others stimulate (Protoporphyrin IX, Mesoporphyrin IX, Hematoporphyrin IX, Deuteroporphyrin IX, Coproporphyrin III, Protoporphyrin IX dimethyl ester, and N-Methylprotoporphyrin IX) guanylyl cyclase (Ignarro, L. J., (1994) Advances in Pharmacology, 26:35–65).

Although porphyrins and metalloporphyrins are known to be useful in the treatment of several diseases and guanylyl cyclase modifiers are known to be useful in the treatment of neurological diseases, there is no teaching or suggestion in the prior art of the present invention.

It is an object of the present invention to provide a method for treating heart failure in mammals by the administration of tetrapyrroles (Tps) or metallotetrapyrroles (MTps).

It is another object of the present invention to provide a method for treating heart failure in mammals comprising administering a Tp or MTp compound such that the compound accumulates in the cardiac myocytes of the mammal.

It is yet another object of the present invention to provide a method for treating heart failure in mammals comprising administering a Tp or MTp compound such that the compound accumulates in the cardiac myocytes at or above a minimum threshold level.

It is still yet another object of the present invention to provide a method for treating heart failure in mammals further comprising readministering the compound once the compound accumulation in the cardiac myocytes drops below a minimum threshold level.

It is a further object of the present invention to provide a method for treating heart failure in mammals comprising administering a Tp or MTp compound such that the compound inhibits guanylyl cyclase activity in the cardiac myocytes.

It is a still further object of the present invention to provide a method for treating heart failure in mammals, where the method comprises administering a Tp or MTp compound in discrete doses and/or in slow, controlled or sustained release doses such that the compound accumulates in the cardiac myocytes in an amount and for a period of time sufficient to allow resolution of heart failure.

It is contemplated that administration of the Tps and MTps of this invention will be ceased upon resolution of the heart failure, heart transplantation, or determination of a suitable stable regimen of treatment not involving these Tps or MTps.

It is also contemplated that the compounds of the present invention may be used in conjunction (either simultaneously, alternately or otherwise) with other compounds typically used for the treatment of heart failure such as, by way of example and without limitation, acetylcholinesterase (ACE) inhibitors, beta-blockers and the like.

It is further contemplated that the compounds of the present invention may be administered with central or peripheral vasodilators such as, by way of example and without limitation, prazocin, hydralazine and the like.

SUMMARY OF THE INVENTION

The present invention is directed to a new method of treating heart failure. Without being held bound by the mechanism of action, the invention presumably accomplishes this goal by providing a method for inhibiting guanylyl cyclase in cardiac myocytes, thereby reducing the rate of formation of cGMP in heart, improving cardiac contractility, and resolving heart failure.

According to one embodiment of the present invention, a method for treating heart failure comprises administering, to a mammal in need of such treatment, a compound of the formula I or the formula II in an amount and for a period of time sufficient to allow accumulation of the compound in the cardiac myocytes.

In another embodiment of the present invention, the method for treating heart failure further comprises maintaining for a sufficient period of time a therapeutically effective amount of a compound of the formula I or the formula II in the cardiac myocytes to increase cardiac contractility.

In another embodiment of the present invention, the method for treating heart failure further comprises ceasing administration of a compound of the formula I or formula II upon resolution of heart failure.

In another embodiment of the invention, the method of treating heart failure comprises:

1) administering to a mammal in need of such treatment, a compound of the formula I or formula II for a period of time and in an amount sufficient to allow accumulation of the compound in cardiac myocytes;
2) maintaining for a period of time a therapeutically effective amount of the compound in the cardiac myocytes to increase cardiac contractility;
3) monitoring cardiac contractility; and
4) ceasing administration of the compound after resolution of heart failure.

The duration and course of administration is important to the present invention, since heart failure may require temporary or prolonged treatment depending on the etiology and planned long-term patient management.

The compounds used in the method of the present invention include compounds of the formula I or formula II and all their isomeric, chiral, pharmaceutically acceptable salt, prodrug, partially unsaturated, completely unsaturated, dimeric, oligomeric, diastereomeric and/or racemic forms wherein:

$RA_1$, $RA_2$, $RB_1$, $RB_2$, $RC_1$, $RC_2$, $RD_1$ and $RD_2$ are independently selected at each occurrence from:
-L-, H, C2–C8 alkenyl, C1–C8 alkyl, C2–C8 alkynyl, formyl, C3–C9 formylalkenyl, C2–C9 formylalkyl, C1–C8 aminoalkyl, C1–C8 hydroxyalkyl, C1–C8 thioalkyl, -carboxy, C2–C8 haloalkyl, C2–C8 carboxyalkyl, (C1–C8)alkoxy-(C1–C8)alkyl, (C1–C8) alkoxy-carbonyl-(C1–C8)alkyl, (C1–C8)alkyl-carbonyl-(C1–C8)alkyl, C2–C12 alkoxycarbonyl, (C1–C8)alkyl-carboxy-(C1–C8)alkyl, (C1–C8)alkyl-carbonyloxy-(C1–C8)alkyl, (C1–C8)alkyl-carbonylamino-(C1–C8)alkyl, (C1–C8)alkyl-carbonylthio-(C1–C8)alkyl, (C1–C8)alkoxy-carbonylamino-(C1–C8)alkyl, aryl(C1–C4)alkyl-oxycarbonylamino-(C1–C8)alkyl, aryl-(C1–C4)alkyl-oxycarbonyloxy-(C1–C8)alkyl, (C1–C8)alkoxy-carbonyloxy-(C1–C8)alkyl, (C1–C8) alkylaminocarbonyl-(C1–C8)alkyl, hydroxy-(C1–C8) alkyloxy-carbonyl-(C1–C8)alkyl, C2–C12 dihydroxyalkyl, aryloxy-(C1–C6)alkyl, aryloxycarbonyl-(C1–C6)alkyl, arylcarbonyloxy-(C1–C8)alkyl, hydroxy substituted carboxy-(C1–C8) alkyl, amino substituted carboxy-(C1–C8)alkyl, thio substituted carboxy-(C1–C8)alkyl, amino acid attached via the amino or carboxyl group, hydroxy acid attached via the hydroxy or carboxyl group, hydroxy substituted amino acid attached via the hydroxy or amino or carboxyl group, pyridinium halide (C2–C8) alkyl, pyridyl-(C2–C8)alkyl, or, $S(=O)_2OR_5$; where, (1) any of the above amine substituted groups is optionally further substituted with an amine protecting group;
(2) any of the above hydroxy substituted groups is optionally further substituted with a hydroxy protecting group;
(3) any of the above carboxy substituted groups is optionally further substituted with a carboxy protecting group; or
(4) any of the pairs of adjacent substituents $RA_1$ and $RA_2$ or $RB_1$ and $RB_2$ or $RC_1$ and $RC_2$ or $RD_1$ and $RD_2$ may join together to form a cyclic group selected from the structures:

where the cyclic group is fused to the respective pyrrole ring to which the adjacent pair of substituents is attached;
$R_3$ and $R_4$ are independently selected at each occurrence from:
carboxy-(C2–C6)alkyl, —$SO_2R_7$, aryl, aryl-(C1–C6) alkyl, cyano or —C(=O)—$NR_5$—C(=O)—;
$R_5$ is independently selected at each occurrence from:
C1–C6 alkyl, H, aryl or aryl-(C1–C6)alkyl;
$R_6$ is independently selected at each occurrence from:
C1–C6 alkyl, H, aryl, aryl-(C1–C6)alkyl or any R6 group may be absent when an M group is coordinated to its corresponding pyrrole ring nitrogen;
R7 is independently selected at each occurrence from:
C6–C10 aryl or C1–C8 alkyl;
-L- is independently selected at each occurrence from:
—$CH(CH_3)$—X—$CH(CH_3)$—, —$CH(CH_3)CH=CH$—, —$CH=CH$—$CH(CH_3)$—, =$CH$—$C(=O)CH(CH_3)$—, —$CH(CH_3)$—$C(=O)CH$= or —$(CH_2)_n$—X—$(CH_2)_n$—; and -L- is attached to two compounds, each compound being independently selected from the compounds of the formula I or formula II to form dimeric or oligomeric forms of said compounds;
M is independently selected at each occurrence from:
Zn, Fe, Mn, Mg, Sn, Co, Ni, Cu, Ca, Ba, Cd, Sr, Ga or Pt; where M may occur more than once in the dimeric or oligomeric forms of the compounds of the formula I or formula II;
X is independently selected at each occurrence from:
—S—, —$NR_5$— or —O—;
n is independently selected at each occurrence from 1, 2, 3 or 4;
aryl is independently selected at each occurrence from:
phenyl, naphthenyl or biphenyl; where said phenyl, naphthenyl or biphenyl groups are independently:
(1) unsubstituted; or
(2) substituted with 1–3 substituents independently selected from: —Fl, —Cl, —Br, —I, C1–C4 alkyl or C1–C4 alkoxy; and
--- is independently saturated or unsaturated at each occurrence as long as the resulting compound is stable.

Exemplary of, and without limitation to, the tetrapyrrole and metallotetrapyrrole compounds useful in the present invention are those disclosed in Aizawa et al. (U.S. Pat. No. 4,997,639), R. T. Gordon (U.S. Pat. No. 4,829,984), Vincent et al. (U.S. Pat. No. 5,422,362), Ignarro, L. J. ((1994) Advances in Pharmacology 26:35–65) and Graczyk et al. (U.S. Pat. No. 5,451,599) the teachings of which are hereby incorporated by reference.

It is understood that some of the compounds of the present invention are known to possess guanylyl cyclase activating rather than inhibiting activity. For those compounds it is contemplated and within the scope of the invention that their structural modification, either by esterification of carboxyl groups, alkylation of the pyrrole nitrogens and/or metallation of the pyrrole nitrogens, will lead to compounds possessing guanylyl cyclase inhibiting activity. Such modifications have already been proven effective (Ignarro, L. J. (1994) Advances in Pharmacology 26:35–65).

It should be understood that although the most important application of this novel therapy is to improve cardiac function in acute heart failure of inflammatory etiology, i.e., myocarditis and acute cardiac rejection associated with cardiac transplantation, therapy with Tps and MTps can be applied to other forms of acute heart failure, such as those induced by chemotherapy, AIDS, or dilated or hypertrophic myopathies, as well as chronic heart failure. Other features, advantages and embodiments of the invention will be apparent to those skilled in the art from the following description, accompanying data and appended claims.

DETAILED DESCRIPTION OF THE INVENTION

Figure 1:
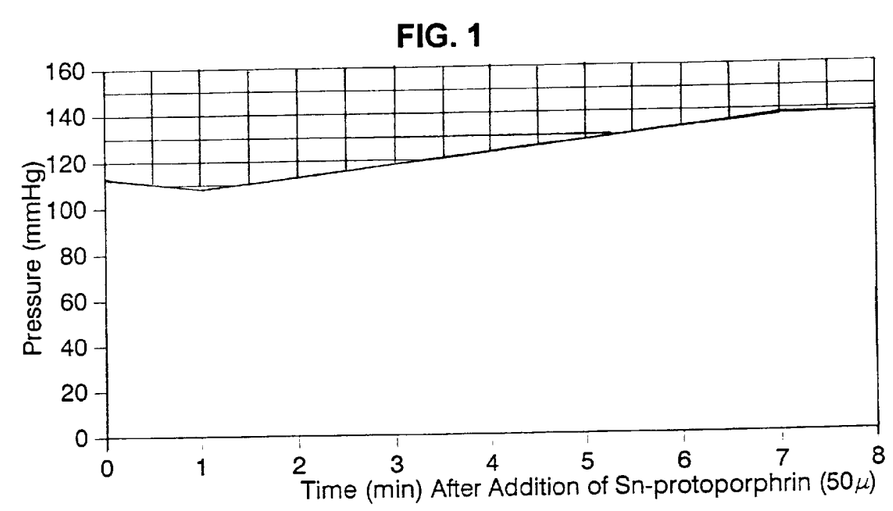
FIG. 1. Representative tracing showing the effect of Sn-protoporphyrin (50 µM concentration in perfusate) on myocarditis in the rat heart model.
Figure 2:
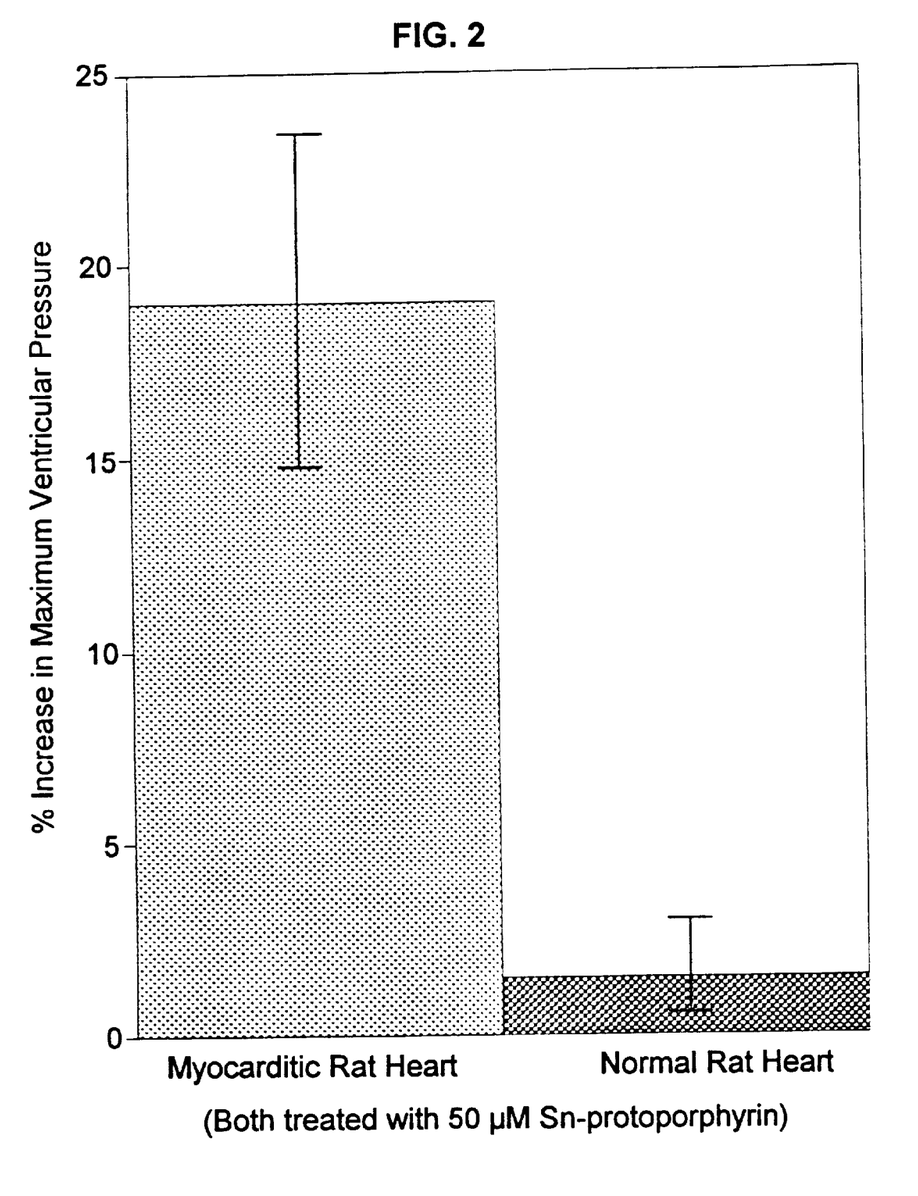
FIG. 2. Effect of Sn-protoporphyrin (50 µM) on contractility in myocarditic vs. normal rat heart.
Figure 3:
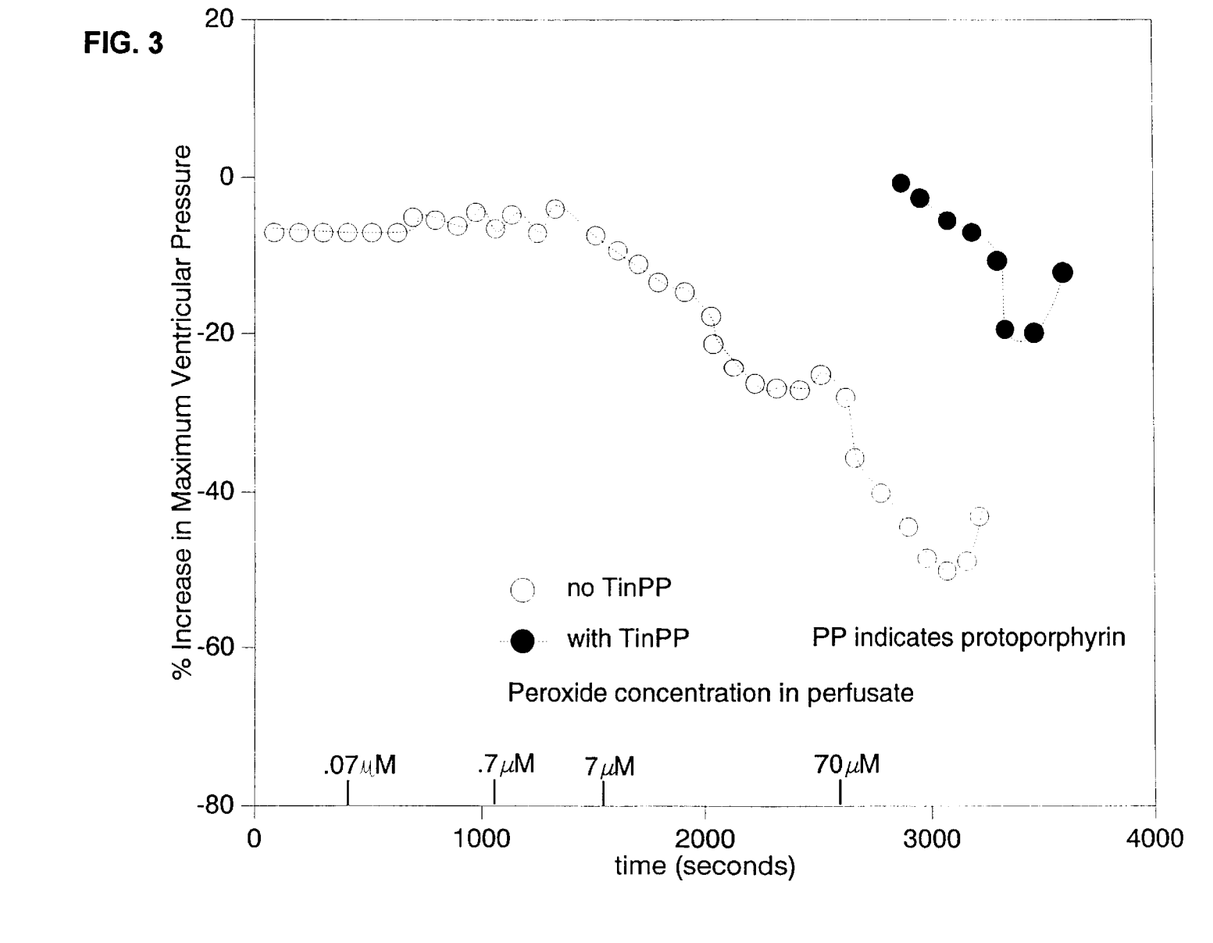
FIG. 3. Sn-protoporphyrin antagonism of $H_2O_2$ induced reduced contractility in rat heart.
Figure 4:
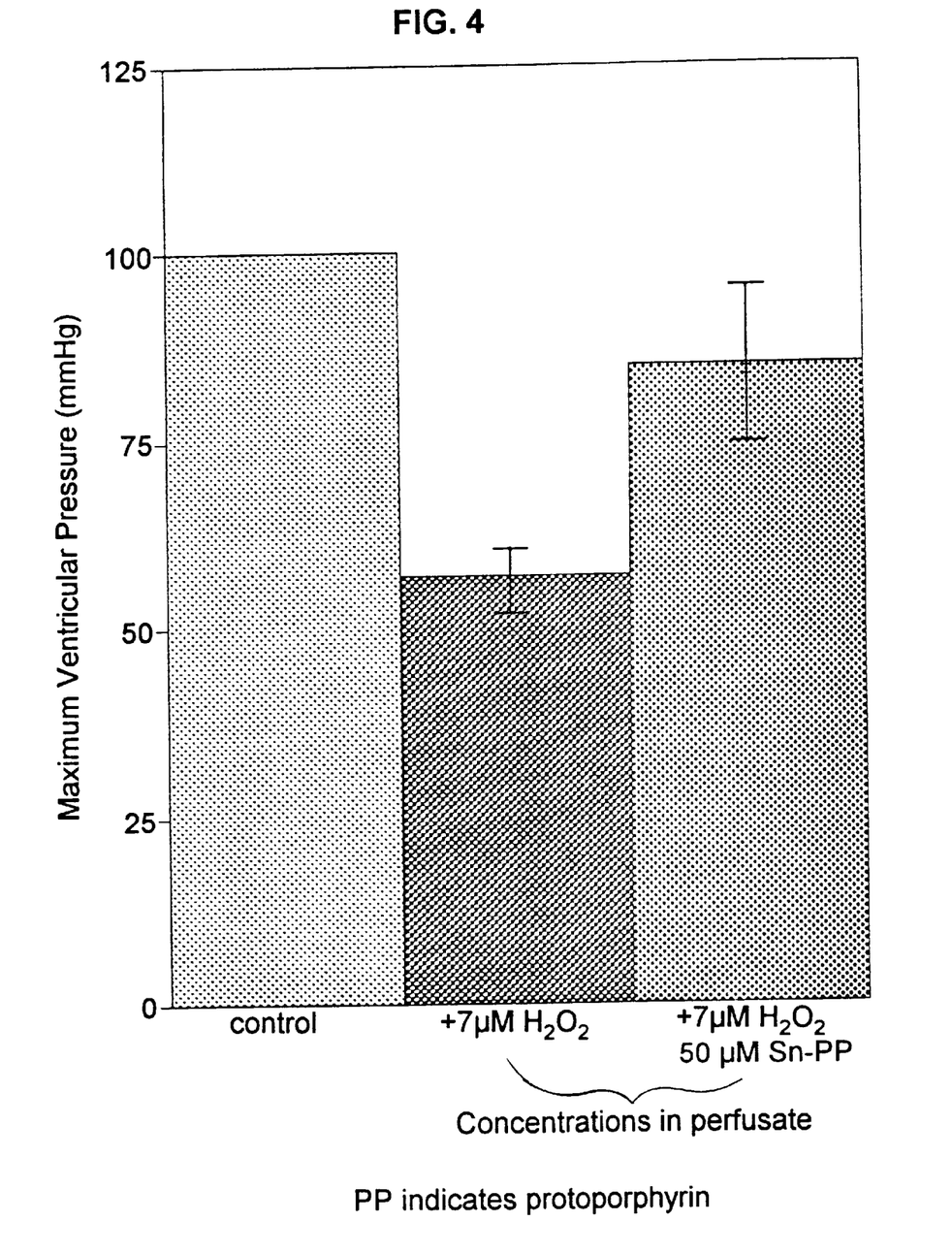
FIG. 4. Time coordinate showing that $H_2O_2$ induced depression of contractility is reversible.

The use of Tps or MTps as direct inhibitors of soluble guanylyl cyclase has a distinct theoretical advantage over indirect inhibition of the enzyme by suppression of NO synthesis or oxidative stress with non-hydrolyzable analogues of arginine and antioxidants. NO and oxidative stress cause arterial vasorelaxation via both cGMP dependent and independent mechanisms. Oxidative stress also has other detrimental effects. Thus, cGMP-independent mechanisms of vasorelaxation are retained with the use of specific inhibitors of guanylyl cyclase but not with inhibitors of the generation of activators of soluble guanylyl cyclase. This affords the benefit that coronary resistance is not increased as much and, as a result, coronary artery perfusion is better maintained.

As used herein, the term "tetrapyrrole" (Tp) refers to all the isomeric, diastereomeric, chiral, racemic, prodrug and pharmaceutically acceptable salt forms of the compounds which are described by formula I above and/or disclosed in Aizawa et al. (U.S. Pat. No. 4,997,639), R. T. Gordon (U.S. Pat. No. 4,829,984), Vincent et al. (U.S. Pat. No. 5,422,362), Ignarro, L. J. ((1994) Advances in Pharmacology 26:35–65) and Graczyk et al. (U.S. Pat. No. 5,451,599) all the teachings of which are hereby incorporated by reference. The TPs of the invention comprise four pyrrole rings held together by methine or methylene carbon bridges, where the bridges are attached to the number 2 or number 5 positions of their respective pyrrole rings. The Tps of the invention may exist as either partially or completely unsaturated systems referred to as porphyrins, chlorins, tetrahydroporphyrins and the like. The Tps and MTps of the invention may also exist in their dimeric or oligomeric forms held together by linkage -L-. L is attached on each side to one Tp or MTp to form a dimeric or oligomeric structure. Conventional methods for the dimerization or oligomerization of porphyrins may be used to prepare these compounds.

As used herein, the term "porphyrin" refers to a completely conjugated tetrapyrrole compound. The porphyrins of the invention may be generally classified as: etioporphyrins, mesoporphyrins, uroporphyrins, coproporphyrins, protoporphyrins, substituted porphyrins, hematoporphyrins, green porphyrins, deuteroporphyrins and photoprotoporphyrins.

As used herein the term "chlorin" refers to a dihydroporphyrin. The chlorins of the invention may be generally classified as: transmesochlorins, chlorins, mesochlorins, isochlorins, mesoisochlorins, bacteriochlorins, acetylchlorins, and formylchlorins. Tetrahydroporphyrins are also contemplated within the scope of the invention.

As used herein, the term "metallotetrapyrrole" (MTp) refers to a tetrapyrrole wherein one or two of the pyrrole nitrogen hydrogen atoms have been replaced with one metal atom. The metals useful in the metalloporphyrins of the invention include: zinc, iron, manganese, magnesium, tin, cobalt, nickel, copper, calcium, barium, cadmium, strontium, gallium and platinum.

As used herein, the term "pyrrole ring" refers to a five membered four carbon and single nitrogen containing ring (as indicated by the letters A, B, C or D in formulae I and II), where the ring may be either saturated or partially or completely unsaturated. Each pyrrole ring will have a substituent attached to its number three position and another substituent attached to its number four position. The methine or methylene carbon bridges used to connect the four pyrrole rings of the Tps and MTps will be attached to the number 2 and number 5 positions of the pyrrole rings.

The compounds used in the method of the present invention are either available commercially or from biological sources or may be prepared as disclosed in Aizawa et al. (U.S. Pat. No. 4,997,639), R. T. Gordon (U.S. Pat. No. 4,829,984), Vincent et al. (U.S. Pat. No. 5,422,362), Ignarro, L. J. ((1994) Advances in Pharmacology 26:35–65), Graczyk et al. (U.S. Pat. No. 5,451,599), U.S. Pat. No. 5,171,749, Cancer Res. 44, 1924 (1989) and ibid 45, 635 (1985). The prodrugs of the compounds may be prepared using conventional synthetic procedures for the modification of functionalized tetrapyrroles. Compounds having chiral carbons may be prepared as individual or a mixture of stereoisomers, such as enantiomers and/or diastereomers. The separation of diastereomers or enantiomers may be effected by conventional means.

As used herein, - - - indicates an either saturated or unsaturated bond. As used herein, indicates an either saturated, partially unsaturated or completely unsaturated pyrrole. As used herein ($R_6$) refers to the optional presence of the $R_6$ group. When a metal M is coordinated to a Tp nitrogen to form a MTp, the nitrogen's corresponding $R_6$ group will be absent. However, the metal M need not coordinate to both available nitrogens in a MTp, and so in a given MTp, one R6 group may be absent while another one is present. The metal in the MTps of the invention may be added to the appropriate Tp using either conventional synthetic methodology or enzymatic methodology, such as by the use of ferrochelatose as described by Jones and Jones (Biochem. J. 113, 507–514 (1969)) or Honeybourne et al. (FEBS Lett. 98, 207–210 (1979)).

During synthetic manipulation, the Tps and MTps may possess protecting groups attached to their amino, carboxyl, hydroxyl, sulfhydryl, carbonyl or other functional groups. The various protecting groups contemplated for the synthetic procedures herein are disclosed in "Protective Groups in Organic Synthesis" (T. W. Greene; John Wiley and Sons, NY, N.Y. 1981) and "The Peptides: Analysis, Synthesis, Biology", Vol. 3 (Academic Press, NY, N.Y. 1981) the disclosures of which are hereby incorporated by reference.

The salt or a corresponding mixture of salts of formula I or formula II can be isolated from the reaction mixture by different methods, e.g. by precipitation, crystallization and other known procedures. A particularly advantageous method consists of addition, to the reaction mixture, of a solvent or of a mixture of low-polarity solvents which, however, form with the solvent used in the reaction a homogeneous solution at a ratio from 1:1 to 1:5. Appropriate solvents include e.g. ethyl, ether or acetone. The resulting mixture is left to stand from several to more than 10 hs for slow precipitation of the product. The precipitate is separated by filtration, washed and dried under vacuum over drying agent, preferably $P_2O_5$. The products are stable and do not deliquesce. They have to be protected from light. The isolation stage possibly comprises separation of the product mixture.

The following abbreviations may also be used herein and are defined as follows:

| Abbreviation | Definition |
|---|---|
| Ala | Alanine |
| Arg | Arginine |
| Asn | Asparagine |
| Asp | Aspartic acid |
| cGMP | guanosine cyclic 3',5'-monophosphate |
| Cys | Cysteine |
| DBA | 2,4-diaminobutyric acid |
| GABA | gamma-aminobutyric acid |
| Gln | Glutamine |
| Glu | Glutamic acid |
| Gly | Glycine |
| GTP | Guanosine triphosphate |
| HEPES | N-[2-hydroxyethyl] piperazine-N'-[2-ethanesulfonic acid] |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| TEA | triethylamine |
| Thr | Threonine |
| Trp | Tryptophan |
| Tyr | Tyrosine |
| Val | Valine |

It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable occurs more than one time in any constituent or formula for a compound, its definition on each occurrence is independent of its definition at every other occurrence. Thus, for example, if a group is shown to be substituted with two $R_5$ groups, then $R_5$ at each occurrence is selected independently from the defined list of possible $R_5$.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. For example, when the substituent is pyrrole unless specified otherwise, said pyrrole group may be bonded to the rest of the compound of a given formula via any atom in such pyrrole group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom to which the substituent is attached are replaced.

The term "amino acid", as used herein, means an organic compound containing both a basic amino group and an acidic carboxyl group. The amino acids used herein may be attached to the rest of the Tp or MTp by either the amino, carboxyl or other functional group present in the amino acid. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) The Peptides, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methylnorleucine, 3,4-dehydroproline, N,N-dimethylaminoglycine, N-methylaminoglycine, 4-aminopiperidine-4-carboxylic acid, 6-aminocaproic acid, trans-4-(aminomethyl) cyclohexanecarboxylic acid, 2-, 3-, and 4-(aminomethyl) benzoic acid, 1-aminocyclopentanecarboxylic acid, 1-aminocyclopropanecarboxylic acid, and 2-benzyl-5-aminopentanoic acid.

The term "amino acid residue", as used herein, means that portion of an amino acid (as defined herein) that is present in a peptide.

As used herein, "alkyl" is intended to include branched, carbocyclic and straight-chain saturated aliphatic hydrocarbon groups having the specified number of carbon atoms; "haloalkyl" is intended to include branched, carbocyclic and straight-chain saturated aliphatic hydrocarbon groups having the specified number of carbon atoms, substituted with 1 or more halogen (for example —$C_vF_w$, where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl, adamantyl and cyclooctyl; and "bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a carbocyclic, straight or branched configuration and one or more unsaturated carbon-carbon bonds which may occur in any stable point along the chain, such as ethenyl, propenyl, and the like; and "alkynyl" is intended to include hydrocarbon chains of either a carbocyclic, straight or branched configuration and one or more triple carbon-carbon bonds which may occur in any stable point along the chain, such as ethynyl, propynyl and the like.

The terms "-(alkyl)-", "-(alkenyl)-", "-(alkynyl)-", "-(phenyl)-", and the like, refer to alkyl, alkenyl, alkynyl and phenyl groups, respectively, which are connected by two bonds to the rest of the structure of Formula (II). Such groups may alternatively and equivalently be denoted as "alkylene", "alkenylene", "phenylene", and the like, respectively.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

"Halo" or "halogen", as used herein, refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl, biphenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl)aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic.

Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "resolution of heart failure" is intended to mean an increase in the strength and/or frequency of myocardial contraction or an increase in the maximum ventricular pressure such that the symptomatology is reduced. It is contemplated that the compounds of the invention may be administered acutely or chronically in order to effect resolution of heart failure.

The tetrapyrroles and metallotetrapyrroles used in the present invention may be administered by a variety of methods. Such methods include, by way of example and without limitation: intraperitoneal, intravascular, intravenous, intracoronary, intramuscular or subcutaneous injection; spray or aerosol for inhalation; or oral, nasal, buccal, rectal or sublingual dosage administration. Such methods of administration and others contemplated within the scope of the present invention are known to the skilled artisan. Such methods of administration are taught in, for example, Kappas et al. (Pediatrics (1988) 81, 485–97), Anderson et al. (Clin. Pharmacol. Ther. (1986) 39, 510–20).

The Tp and MTp derivatives should be readministered when contractility lessens after the preceding dose, which may depend on the derivative used. Contractility may be measured by either invasive or noninvasive methods such as catheterization, echocardiography, nuclear medicine, ultrasound imaging, blood pressure, magnetic resonance imaging and clinical signs of heart failure (edema, shortness of breath, etc.). The continued readministration of Tp and MTp derivatives serves to replace previously administered Tp, which is cleared over time, to ensure that soluble guanylyl cyclase is inhibited. Since the Tp and MTp derivatives are believed to inhibit soluble guanylyl cyclase by displacing the naturally occurring heme moiety in soluble guanylyl cyclase (Ignarro, L. J. (1994) Advances in Pharmacology 26:35–65), inhibition by some compounds may be less reversible and the inhibition longer lasting. Therefore, the necessity for or frequency of readministration for chronic or prolonged inhibition of soluble guanylyl cyclase may be different for various Tp and MTp derivatives.

Although there is no specific way to target Tps and MTps given intravenously exclusively to the heart, systems or forms of Tps and MTps which are subsequently created and target themselves to the heart, i.e., preferentially accumulate in the myocardium, will be especially useful for the treatment of heart failure.

The Tps and MTps used in the present invention may be formulated in a variety of ways. For injection, the compounds may be formulated, for reconstitution with an appropriate solution, as, for example and without limitation: freeze dried, rotary dried or spray dried powders; amorphous or crystalline powders; or granules, precipitates or particulates. For injection, the compounds may also be formulated as suspensions or liquids in the appropriate solutions, such as, by way of example and without limitation, water, aqueous solvents, nonprotic solvents, protic solvents, hydrophilic solvents, hydrophobic solvents, polar solvents, nonpolar solvent and/or combinations thereof, optionally containing stabilizers, pH modifiers, surfactants, bioavailability modifiers and/or combinations thereof. The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for examples, Silastic, silicone rubber-manufactured by the Dow-Corning Corporation.

For inhalation either nasally or orally, the compounds of the invention may be formulated as sprays or aerosols containing the appropriate solvents (such as water, aqueous, nonaqueous, polar, nonpolar, hydropic, hydrophilic and/or combinations thereof) and optionally other compounds (stabilizers, perfumes, antimicrobial agents, antioxdants, pH modifiers, surfactants and/or bioavailability modifiers) to render the compounds of the invention either partially or completely soluble. A propellant such as compressed air, nitrogen, carbon dioxide or hydrocarbon based low boiling solvents (such as butane, propane or others) would be used in an aerosol formulation.

For nasal administration, the same type of formulations used for the inhalation administration may be used. In addition, ointments or creams containing the compounds of the invention may also be used. It is contemplated that bioavailability enhancers such as alcohols or other compounds that enhance the penetration of the Tps and MTps into the nasal mucosa may be needed to prepare suitable formulations for nasal administration.

For oral, buccal, and sublingual administration, the compounds of the invention may be administered as either solutions or suspensions in the form of gelcaps, caplets, tablets, capsules or powders. For rectal administration, the compounds of the invention may be administered in the form of suppositories, ointments, tablets and creams for release of compound in the large intestine, sigmoid flexure and/or rectum. It is contemplated that the compounds may be formulated as for example and without limitation: freeze dried, rotary dried or spray dried powders; amorphous or crystalline powders; or granules, precipitates or particulates. The solids used may be either free-flowing or compressed. The compounds may also be formulated as ointments, creams, gels, slurries, suspensions or liquids in solutions, such as, by way of example and without limitation, water, aqueous solvents, nonprotic solvents, protic solvents, hydrophilic solvents, hydrophobic solvents, polar solvents, nonpolar solvent, emollients and/or combinations thereof, optionally containing stabilizers, pH modifiers, surfactants, perfumes, astringents, cosmetic foundations, pigments, dyes, bioavailability modifiers and/or combinations thereof.

The compounds may also be formulated as liposomes. They may be either included within or attached to the surface of the liposomes. Suitable methods for preparing liposomes are well known in the art and inclusion of Tps and MTps into them may be accomplished as described in U.S. Pat. No. 5,214,036.

In solid unit dosage forms the compounds can be combined with conventional carriers, for example, binders, such as acacia, corn starch or gelatin; disintegrating agents, such as, corn starch, guar gum, potato starch or alginic acid; lubricants, such as, stearic acid or magnesium stearate; and inert fillers, such as lactose, sucrose or corn starch.

The term "unit dosage form" is used herein to mean a single or multiple dose form containing a quantity of the active ingredient and the diluent or carrier, said quantity being such that one or more predetermined units are normally required for a single therapeutic administration. In the case of multiple dose forms, such as liquids or scored tablets, said predetermined unit will be one fraction such as 5 ml (teaspoon) quantity of a liquid or a half or quarter of a scored tablet, of the multiple dose form.

The compounds of general Formulas I or II may also be administered as liquid suspensions or solutions using a sterile liquid, such as an oil, water, an alcohol, or mixtures thereof, with or without the addition of a pharmaceutically suitable surfactants, suspending agent, or emulsifying agent for oral or parenteral administration.

For liquid preparations, the compounds of Formula I or Formula II can be formulated suitably with oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glyceridees and acetylated fatty acid glycerides; with alcohols, such as ethanol, isopropanol, hexadecyl alcohol, glycerol and propylene glycol; with glycerol ketals, such as 2,2-dimethyl-1, 3-dioxolane-4-methanol; with ethers, such as poly (ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Oils can also be employed in the preparation of formulations of the soft gelatin type and suppositories. Water, saline, aqueous dextrose and related sugar solutions, and glycerols, such as polyehtyleneglycol, may be employed in the preparation of liquid formulations which may suitably contain suspending agents, such as pectin, carbomers, methyl cellulose, hydroxypropyl cellulose or carboxymethyl cellulose, as well as buffers and preservatives. Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and polyoxyethylenepolyoxypropylene copolymers; and amphoteric detergents, for example, alkyl β-aminopropionates and 2-alkylimidazoline quaternary ammonium salts; and mixtures thereof. Since maintenance of a threshold level of Tps or MTps in the cardiac myocytes is an important aspect of the invention, it is contemplated that either one or a combination of short-acting, long-acting, sustained release, controlled release, pulsated release or slow release dosage forms may be used in the present invention. It is contemplated that between administrations the level of compound in a subject's cardiac myocytes may fall below a desired threshold level. In such cases, the method of the present invention will remain effective as long as the compound level in the subject is above the threshold level for the majority of the time required for a dosing regimen. The course and duration of administration of and the dosage requirements for the compounds of the present invention will vary according to the subject being treated, the compound being administered, the formulation used, the method of administration used, the severity and type of the heart failure being treated, and the coadministration of other drugs and other factors.

The artisan administering the compounds of the invention will use increased cardiac contractility or improved cardiovascular function/physiology as an indicator of the dosage regimen required to practice the present invention on any given subject. Since subject-to-subject variability will occur, the artisan will be required to measure cardiac contractility or index thereof and continue administering the compound of the invention until the desired level of contractility is achieved. Alternately, the artisan may measure the level (amount or concentration) of compound of the invention in the subject's cardiac myocyte or blood and continue administration of the compound until the desired level in the myocyte or blood is achieved. Generally, blood level amounts of 25–50 micromole/liter of a compound of the invention will result in an observable increase in cardiac contractility. The amount of effective compound administered will vary over a wide range and can be any effective amount. Depending on the patient to be treated, the severity of the condition being treated and the mode of administration, the effective amount of compound administered will vary from about 0.1 mg/kg to 500 mg/kg of body weight of the subject per day. It is contemplated that some compounds will require higher or lower blood levels to effect an observable increase in cardiac contractility.

It is contemplated, for purposes of this invention, that a tetrapyrrole or metallotetrapyrrole can be administered to a subject in conjunction with other therapeutical methods or in combination with other compounds known in the art to be useful for heart failure therapy. When administered in conjunction with such other compounds, those compounds may be administered either before, during or after administration of the tetrapyrroles or metallotetrapyrroles of the invention. For example, a compound of the formula I or the formula II can be administered in conjunction with, by way of example and without limitation, central or peripheral vasodilators, acetylcholinesterase inhibitors or beta-blockers. Some exemplary compounds contemplated as useful in combination therapy include prazocin, hydralazine and the like. When such combination therapy is employed for the treatment of heart failure, the compounds may be administered at a dosage known in the art to be effective for treating heart failure. It is possible, combination therapy will produce an additive or synergistic effect. In combination therapy, the compounds may, therefore, be administered at a lower dosage level or at less frequent intervals as compared to when used alone.

The compounds may be formulated as their pharmaceutically acceptable salts. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a predetermined amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein the term "prodrug form" means that form of a Tp or MTp that when administered to a subject will be modified to the Tp or MTp drug form having the desired therapeutic effect. Generally, Tp and MTp prodrugs will possess functional groups which may undergo either one or a combination of hydrolysis, reduction, oxidation, alkylation, dealkylation or other modification caused by either one or a combination of chemicals, biochemicals, enzymes, or metabolic and/or catabolic pathways present in a subject receiving the prodrug to form a Tp or MTp drug having the desired therapeutic profile. By way of example and without limitation, an esterified form of a Tp is considered prodrug if, when it is administered to a subject, the ester is hydrolyzed leaving the unesterified Tp having the desired pharmaceutical activity. It is understood and within the scope of the present invention that the prodrugs themselves may possess some desirable therapeutic effect.

The following types of Tp and MTp prodrugs are, without limitation to, exemplary of those contemplated within the scope of the present invention: esters, amides, thioesters and thioamides of Tps or MTps having a carboxyl group; carbonates, carbamates, carboxyl esters, phosphate esters, sulfate esters, thioesters, ethers, thioethers, acetals or ketals of Tps or MTps having a hydroxyl group; amides, thioamides, carbamates, ureas, thioamides, nitrosos, nitrates and benzyl derivatives of Tps and MTps having an amine group; and sulfones, sulfonates, sulfoniums and benzyl derivatives of Tps or MTps having a sulhydryl group.

As used herein, the term "amine protecting group" (or "N-protected") refers to any group known in the art of organic synthesis for the protection of amine groups. As used herein, the term "amine protecting group reagent" refers to any reagent known in the art of organic synthesis for the protection of amine groups which may be reacted with an amine to provide an amine protected with an amine protecting group. Such amine protecting groups include those listed in Greene and Wuts, "Protective Groups in Organic Synthesis" John Wiley & Sons, New York (1991) and "The Peptides: Analysis, Synthesis, Biology", Vol. 3, Academic Press, New York (1981), the disclosure of which is hereby incorporated by reference. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10-dioxo-10,10,10,10-tetrahydrothio-xanthyl)]methyloxycarbonyl; 2-trimethylsilylethyloxycarbonyl;

2-phenylethyloxycarbonyl; 1,1-dimethyl-2,2-dibromoethyloxycarbonyl; 1-methyl-1-(4-biphenylyl) ethyloxycarbonyl; benzyloxycarbonyl; p-nitrobenzyloxycarbonyl; 2-(p-toluenesulfonyl) ethyloxycarbonyl; m-chloro-p-acyloxybenzyloxycarbonyl; 5-benzyisoxazolylmethyloxycarbonyl; p-(dihydroxyboryl) benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; or methanesulfonamide.

As used herein, the term "carboxyl protecting group" refers to any group known in the art of organic synthesis for the protection of carboxyl groups. Such carboxyl protecting groups include those listed in Greene and Wuts, "Protective Groups in Organic Synthesis" John Wiley & Sons, New York (1991) and "The Peptides: Analysis, Synthesis, Biology", Vol. 3, Academic Press, New York (1981), the disclosure of which is hereby incorporated by reference. Examples of carboxyl protecting groups include, but are not limited to, the following: 1) substituted methyl ester type such as methoxymethyl, tetrahydropyranyl, benzyloxymethyl, N-phthalimidomethyl; 2) 2-substituted ethyl ester type such as 2,2,2-trichloroethyl, 2-methylthioethyl, t-butylethyl, cinnamylethyl, benzylethyl, 2-(2'-pyridyl)ethyl; 3) substituted benzyl ester type such as triphenylmethyl, 9-anthrylmethyl, p-nitrobenzyl, 4-picolyl, 2,4,6-trimethylbenzyl; 4) silyl ester type such as trimethylsilyl, t-butyldimethylsilyl, phenyldimethylsilyl; 5) miscellaneous type such as oxazole, orthoester; 6) amides type such as N,N-dimethyl, piperidinyl, pyrrolindinyl; and 7) hydrazide type such as alkylated hydrazides.

As used herein, the term "hydroxy protecting group" (or "O-protected") refers to any group known in the art of organic synthesis for the protection of hydroxyl groups. As used herein, the term "hydroxy protecting group reagent" refers to any reagent known in the art of organic synthesis for the protection of hydroxy groups which may be reacted with an hydroxy to provide an hydroxy group protected with an hydroxy protecting group. Such protecting groups include those listed in Greene and Wuts, "Protective Groups in Organic Synthesis", John Wiley & Sons, New York (1991), the disclosure of which is hereby incorporated by reference. The hydroxy protecting groups are base-stable and can include, but are not limited to acyl types, aromatic carbamate types and alkyl types. Exemplary are methyl, methoxymethyl (MOM), methylthiomethyl, benzyloxymethyl, t-butoxymethyl, 2-methoxyethoxymethyl, 2,2,2-trichloroethoxymethyl, 2-(trimethylsilyl)ethoxymethyl (SEM), tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

Suitable hydroxy protecting groups may include the following protecting groups as ethers: tetrahydropyranyl, triphenylmethyl, benzyl, tetrahydrofuranyl, allyl, methoxymethyl (MOM), benzyloxymethyl, p-methoxybenzyloxymethyl, 2-trimethylsilylethoxymethyl (SEM), t-butoxymethyl, methylthiomethyl, 2-methoxyethoxymethyl, trichloroethoxymethyl, t-butyl, p-methoxybenzyl, t-butyldimethylsilyl, o-nitrobenzyl, p-methoxyphenyldiphenylmethyl, p-nitrobenzyl, triisopropylsilyl, t-butyldiphenylsilyl.

Preferred Embodiments

The preferred tetrapyrroles and metallotetrapyrroles used in the method of the present invention are those compounds of the formula I or formula II, and all their isomeric, chiral, pharmaceutically acceptable salt, prodrug, partially unsaturated, completely unsaturated, dimeric, oligomeric, diastereomeric and/or racemic forms wherein:

$RA_1$, $RA_2$, $RB_1$, $RB_2$, $RC_1$, $RC_2$, $RD_1$ and $RD_2$ are independently selected at each occurrence from:

-L-, H, C2–C8 alkenyl, C1–C8 alkyl, formyl, C3–C9 formylalkenyl, C2–C9 formylalkyl, C1–C8 hydroxyalkyl, C1–C8 thioalkyl, -carboxy, C2–C8 haloalkyl, C2–C8 carboxyalkyl, (C1–C8)alkoxy-(C1–C8)alkyl, (C1–C8)alkoxy-carbonyl-(C1–C8) alkyl, (C1–C8)alkyl-carbonyl-(C1–C8)alkyl, C2–C12 alkoxycarbonyl, (C1–C8)alkyl-carboxy-(C1–C8)alkyl, (C1–C8)alkyl-carbonyloxy-(C1–C8)alkyl, (C1–C8) alkyl-carbonylamino-(C1–C8)alkyl, (C1–C8)alkyl-carbonylthio-(C1–C8)alkyl, aryl-(C1–C4)alkyl-oxycarbonyloxy-(C1–C8)alkyl, (C1–C8)alkoxy-carbonyloxy-(C1–C8)alkyl, hydroxy-(C1–C8) alkyloxy-carbonyl-(C1–C8)alkyl, C2–C12 dihydroxyalkyl, aryloxy-(C1–C6)alkyl, aryloxycarbonyl-(C1–C6)alkyl, arylcarbonyloxy-(C1–C8)alkyl, hydroxy substituted carboxy-(C1–C8) alkyl, amino substituted carboxy-(C1–C8)alkyl, this substituted carboxy-(C1–C8)alkyl, amino acid attached via the amino or carboxyl group, hydroxy acid attached via the hydroxyl or carboxyl group, hydroxy substituted amino acid attached via the hydroxy or amino or carboxyl group, pyridinium halide (C2–C8) alkyl, pyridyl-(C2–C8)alkyl, or, $S(=O)_2OR_5$; where, (1) any of the above amine substituted groups is optionally further substituted with an amine protecting group;

(2) any of the above hydroxy substituted groups is optionally further substituted with a hydroxy protecting group;

(3) any of the above carboxy substituted groups is optionally further substituted with a carboxy protecting group; or (4) any of the pairs of adjacent substituents $RA_1$ and $RA_2$ or $RB_1$ and $RB_2$ or $RC_1$ and $RC_2$ or $RD_1$ and $RD_2$ may join together to form a cyclic group selected from the structures:

where the cyclic structure is fused to the respective pyrrole ring to which the adjacent pair of substituents is attached; and M is independently selected at each occurrence from:

Zn, Fe, Mn, Mg, Sn, Co, Ni, Cu, Ca, Ba or Cd; where M may occur more than once in the dimeric or oligomeric forms of the compounds of the formula I or formula II.

The more preferred Tps and MTps used in the method of the present invention are those preferred compounds of the formula I or formula II, and all their isomeric, chiral, pharmaceutically acceptable salt, prodrug, chlorin, porphyrin, dimeric, oligomeric, diastereomeric and/or racemic forms wherein:

$RA_1$, $RA_2$, $RB_1$, $RB_2$, $RC_1$, $RC_2$, $RD_1$ and $RD_2$ are independently selected at each occurrence from:

-L-, H, C2–C8 alkenyl, C1–C8 alkyl, formyl, C2–C8 haloalkyl, C1–C8 thioalkyl, C3–C9 formylalkenyl, C2–C9 formylalkyl, C1–C8 hydroxyalkyl, -carboxy, C2–C8 carboxyalkyl, (C1–C8)alkoxy-(C1–C8)alkyl, (C1–C8)alkoxy-carbonyl-(C1–C8)alkyl, (C1–C8)alkyl-carboxy-(C 1–C8)alkyl, (C1–C8)alkyl-carbonyloxy-(C1–C8)alkyl, aryl-(C1–C4)alkoxy-carbonyloxy-(C1–C8)alkyl, (C1–C8)alkoxy-carbonyloxy-(C1–C8)alkyl, hydroxy-(C1–C8)alkyloxy-carbonyl-(C1–C8)alkyl, C2–C12 dihydroxyalkyl, aryloxy-(C1–C6)alkyl, aryloxycarbonyl-(C1–C6)alkyl, arylcarbonyloxy-(C1–C8)alkyl, hydroxy substituted carboxy-(C1–C8)alkyl, amino acid attached via the amino or carboxyl group, hydroxy acid attached via the hydroxyl or carboxyl group, pyridinium halide (C2–C8) alkyl, pyridyl-(C2–C8)alkyl, or, $S(=O)_2OR_5$; where, (1) any of the above amine substituted groups is optionally further substituted with an amine protecting group;

(2) any of the above hydroxy substituted groups is optionally further substituted with a hydroxy protecting group;

(3) any of the above carboxy substituted groups is optionally further substituted with a carboxy protecting group;

(4) any of the pairs of adjacent substituents $RA_1$ and $RA_2$ or $RB_1$ and $RB_2$ or $RC_1$ and $RC_2$ or $RD_1$ and $RD_2$ may join together to form a cyclic group selected from the structures:

where the cyclic structure is fused to the respective pyrrole ring to which the adjacent pair of substituents is attached; and (5) the amino acid is independently selected at each occurrence from:

Ala, Arg, Asn, Asp, Cys, DBA, GABA, Gln, Glu, Gly, HB, Ile, Leu, Lys, Met, Phe, Pro, Ser, Thr, Trp, Tyr and Val; and M is independently selected at each occurrence from:

Zn, Fe, Mn, Mg, Sn, Ca or Ba; where M may occur more than once in the dimeric or oligomeric forms of the compounds of the formula I or formula II.

The most preferred Tps and MTps used in the method of the present invention are those more preferred compounds of the formula I or formula II, and all their isomeric, chiral, pharmaceutically acceptable salt, prodrug, chlorin, porphyrin, dimeric, oligomeric, diastereomeric and/or racemic forms wherein:

$RA_1$, $RC_1$ and $RD_2$ are independently selected at each occurrence from H or —$CH_3$;

$RA_2$ and $RB_2$ are independently selected at each occurrence from:

—$CH(OR_5)CH_3$—, -L-, —$CH_2CH_3$, —CH=$CH_2$, —$CH_2CO_2R_5$, —C(=O)H, —$CH_2CH_2CH_3$, H, =CH—C(=O)H, —CH(SH)$CH_3$, —CH(Br)$CH_3$, —CH($OR_5$)$CH_2OR_5$, pyridinium halide (C2–C8) alkyl, pyridyl-(C2–C8)alkyl, or —$SO_3R_5$;

$RB_1$ is formyl or H;

$RC_2$ and $RD_1$ are independently selected at each occurrence from:

—$CH_2CH_2CO_2R_5$, —$CH_2CO_2R_5$, —$CO_2R_5$, —$CH_2CH_2CH_3$ or H; and

M is independently selected at each occurrence from:

Zn, Fe, Mn, Mg or Sn; and M may occur more than once in the dimeric or oligomeric forms of the compounds of the formula I or formula II.

The specifically preferred Tps and MTps used in the method of the present invention are those most preferred compounds of the formula I or formula II, and all their isomeric, chiral, pharmaceutically acceptable salt, prodrug, porphyrin, dimeric, oligomeric, diastereomeric and/or racemic forms selected from:

deuteroporphyrin IX disulfonate, deuteroporphyrin IX bisglycol, coproporphyrin I, hematoporphyrin IX dimethyl ester, hematoporphyrin IX, deuteroporphyrin IX dimethyl ester, N-phenylproto-porphyrin IX, Ferro-protoporphyrin IX, Zinc-protoporphyrin IX, Manganese-protoporphyrin IX and Tin-protoporphyrin IX.

The preferred pharmaceutical salts for the compounds of the present invention are those selected from the group consisting of:

hydrochloric, hydrobromic, sulfuric, sulfonic, sulfamic, phosphoric, nitric, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and amino acids.

The preferred method of treating heart failure comprises:

1) administering to a mammal in need of such treatment, a compound of the formula I or formula II for a period of time and in an amount sufficient to allow accumulation of the compound in cardiac myocytes;

2) maintaining for a period of time a therapeutically effective amount of the compound in the cardiac myocytes to increase cardiac contractility;

3) monitoring cardiac contractility at any time; and 4) ceasing administration of the compound after resolution of heart failure.

The preferred method of administration for the Tps and MTps of the present invention is infusion or injection. The more preferred method of administration is intravascular, intracoronary, intravenous, and intramuscular injection. The most preferred method for administration to the heart is intravenous since this is a route of easy access and will lead to perfusion, via coronary arteries, which perfuse all cardiac myocytes.

All chemicals were purchased from Sigma Chemicals (St. Louis, Mo.) unless otherwise noted.

EXAMPLES

1. Administration of Sn-Protoporphyrin in Experimental Myocarditis

Male Wistar rats were purchased from Charles River (Wilmington, Mass.). The rats were caged in groups of three with food and water ad libitum under an artificial light-dark cyclase of twelve hours.

Experimental myocarditis was induced in the rats by intraperitonal injection (IP) of 5 mg/kg isoproterenol 48 hours. The presence of myocarditis was confirmed in a separate set of parallel hearts using microscopy and hematoxylin-eosin staining by the presence of inflammatory cells and myocyte necrosis.

Rats were anesthetized using Ketamine and the hearts excised and placed in cooled Tyrode buffer solution (144 mM NaCl, 5 mM KCl, 0.9 mM $MgCl.6H_2O$, 6 mM Hepes, 15 mM Glucose, and 1.5 mM $CaCl_2$). The hearts were perfused using a non-recirculating Langendorf technique. The left ventricle was vented using a 22 gauge catheter. A fluid filled balloon was inserted into the left ventricle by incising the left atrium and placing the balloon through the mitral valve opening. The balloon was secured and the opening secured using a purse string. The heart was retrograde perfused through the aorta with Tyrode buffer (water, 144 mM NaCl, 5 mM KCl, 0.09 mM MgCl hexahydrate, 6 mM HEPES, 15 mM glucose and 1 mM $CaCl_2$) solution (pH 7.4, 37° C.) at constant volume. The buffer solution was bubbled using a 100% $O_2$ gas. The heart was perfused at a constant rate through a cannula placed in the aorta. The systolic and diastolic pressures were recorded on one channel through the balloon using a Gould WindoGraf oscillograph-chart recorder. The balloon was zeroed to a volume 0.1 ml. At this volume, the diastolic pressure was zero. Hearts were equilibrated for 30–45 minutes until contractility stabilized.

50 uM (Sn-protoporphyrin) was added to the perfusing buffer. Maximum left ventricular pressure was increased (above baseline levels) by 22% (n=3). The increase in contractility occurred within 2 minutes of infusion of Sn-protoporphyrin. This was accompanied by an approximately 10% decrease in aortic perfusion pressure. Furthermore, Sn-protoporphyrin had no effect on contractility or aortic perfusion pressure in normal rat hearts (n=3).

The results described in this study clearly demonstrate that Sn-protoporphyrin is a potent positive inotropic agent in a rat model of myocarditis. Overall, a twenty-two (22% +/−2.6%) increase in maximum left ventricular pressure was obtained at the approximate dose as used in the treatment of other diseases in humans (Anderson, K. E. et al. (1986) Clin. Pharmacol. Ther. 39:510–20), whereas no effect was documented in normal rat hearts. There was also an approximately 10% decrease in the aortic perfusion pressure in the myocarditic hearts, suggesting that coronary resistance is decreased.

2. Administration of Sn-protoporphyrin to Hearts Perfused with $H_2O_2$

Male Wistar rats were purchased from Charles River (Wilmington, Mass.). The rats were caged in groups of three with food and water ad libitum under an artificial light-dark cyclase of twelve hours.

Rats were anesthetized using Ketamine and the hearts excised and placed in cooled Tyrode buffer solution (water, 144 mM NaCl, 5 mM KCl, 0.9 mM $MgCl.6H_2O$, 6 mM Hepes, 15 mM Glucose, and 1.5 mM $CaCl_2$). The hearts were perfused using a non-recirculating Langendorff technique. The left ventricle was vented using a 22 gauge catheter. A fluid filled balloon was inserted into the left ventricle by incising the left atrium and placing the balloon through the mitral valve opening. The balloon was secured and the opening secured using a purse string. The heart was retrograde perfused through the aorta with Tyrode buffer solution (pH 7.4, 37° C.) at constant volume. The buffer solution was bubbled using a 100% $O_2$ gas. The heart was perfused at a constant rate through a cannula placed in the aorta. The systolic and diastolic pressures were recorded on one channel through the balloon using a Gould WindoGraf oscillograph-chart recorder. The balloon was zeroed to a volume 0.1 ml. At this volume, the diastolic pressure was zero. Hearts were equilibrated for 30–45 minutes until contractility stabilized.

The effect on maximum left ventricular pressure of adding increasing concentrations of $H_2O_2$ to the buffer was measured. 70 nM–70 uM $H_2O_2$ decreased contractility in a concentration dependent manner. Maximum depression of systolic pressure was approx 40%. Myocardial depression was reversible up to a $H_2O_2$ concentration of 100 uM (not shown). Myocardial depression by $H_2O_2$ was reduced (p<0.05) by approximately 50% when hearts were perfused with Sn-protoporphyrin, a potent inhibitor of soluble guanylyl cyclase, for 15 minutes prior to perfusion with $H_2O_2$.

The results described in this study clearly demonstrate that Sn-protoporphyrin inhibits myocardial depression by the oxidant $H_2O_2$. This suggests that Sn-protoporphyrin can inhibit myocardial contractile depression caused by oxidants.

The above is a detailed description of a particular embodiment of the invention. It is recognized that departures from the disclosed embodiment may be made within the scope of the invention and that obvious modifications will occur to a person skilled in the art.

The full scope of the invention is set out in the claims that follow and their equivalents. Accordingly, the claims and specification should not be construed to unduly narrow the full scope of protection to which the invention is entitled.

3. Administration of 1H-[1,2,4]Oxadiazolo[4,3-a]quinoxalin-1-one to Hearts Perfused with $H_2O_2$ Male Wistar rats were purchased from Charles River (Wilmington, Mass.). The rats were caged in groups of three with food and water ad libitum under an artificial light-dark cyclase of twelve hours.

Rats were anesthetized using Ketamine and the hearts excised and placed in cooled Tyrode buffer solution (water, 144 mM NaCl, 5 mM KCl, 0.9 mM $MgCl.6H_2O$, 6 mM Hepes, 15 mM Glucose, and 1.5 mM $CaCl_2$). The hearts were perfused using a non-recirculating Langendorff technique. The left ventricle was vented using a 22 gauge catheter. A fluid filled balloon was inserted into the left ventricle by incising the left atrium and placing the balloon through the mitral valve opening. The balloon was secured and the opening secured using a purse string. The heart was retrograde perfused through the aorta with Tyrode buffer solution (pH 7.4, 37° C.) at constant volume. The buffer solution was bubbled using a 100% $O_2$ gas. The heart was perfused at a constant rate through a cannula placed in the aorta. The systolic and diastolic pressures were recorded on one channel through the balloon using a Gould WindoGraf oscillograph-chart recorder. The balloon was zeroed to a volume 0.1 ml. At this volume, the diastolic pressure was zero. Hearts were equilibrated for 30–45 minutes until contractility stabilized.

The effect on maximum left ventricular pressure of adding increasing concentrations of $H_2O_2$ to the buffer was measured. 70 nM–70 uM $H_2O_2$ decreased contractility in a concentration dependent manner. Maximum depression of systolic pressure was approx 40%. Myocardial depression was reversible up to a $H_2O_2$ concentration of 100 uM (not shown). Myocardial depression by peroxide after ten minutes was inhibited by almost 100% when hearts were concurrently perfused with 1H-[1,2,4]Oxadiazolo[4,3-a]quinoxalin-1-one (ODQ), a potent new and specific inhibitor of soluble guanylyl cyclase (B. Mayer, Molecular Pharmacology 48: 184–188).

The results described in this study clearly demonstrate that ODQ increased contractility in myocarditic hearts by 20.8±4.2%(n=4,p<0.05), and inhibits myocardial depression by the oxidant $H_2O_2$. This suggests that inhibitors of soluble guanylyl cyclase can reverse myocardial contractile depression caused by oxidants.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

4. Preparation of a Formulation for Injection

Zn-protoporphyrin (0.75 micromoles into 0.25 mL) is dissolved in sterile aqueous phosphate buffer (1 mL, 0.2 M, $Na_3PO_4.12 H_2O$) and the pH adjusted to 7.5–7.8 with 0.3 N HCl. The solution is filtered through a 0.2 micron filter and transferred (2.0 mL) to a sterile bottle. The solution is diluted so as to deliver 0.5–0.75 micrograms per kilogram of body weight. The solution, is stored at 4° C. in the dark and equilibrated at room temperature in subdued light immediately before use.

5. Preparation of a Formulation for Hard Gelatin Capsules

Zn-protoporphyrin (50–500 mg) is mixed with talc (1–100 mg) and lactose (1–200 mg). The powders are mixed and passed through a fine mesh screen. The powder is then filled into hard gelatin capsules at a net fill of 60–800 mg per capsule.

6. Preparation of a Formulation for Tablets

Zn-protoporphyrin (50–700 mg) is mixed with starch (10–200 mg) and lactose (10–200 mg). After granulation, magnesium stearate (1–20 mg) is added and the powders mixed and screened. The mixture is then compressed into tablets weighing 75–1000 mg each.

7. Preparation of a Formulation for Injection

A sterile solution containing the following amounts of the listed components is prepared: Zn-protoporphyrin (1–20% w/w), water (70–99% w/w), polyvinylpyrrolidone (0.0–5.0% w/w), alcohol (0.0–10.0% w/w), lecithin (0.0–2.5% w/w), HCl (as needed to adjust pH), buffer (0.01–100 mM) and NaCl (0.0–250 mM). The solution is placed in sealed ampules and stored with refrigeration in the dark.

8. Preparation of a Formulation for Oral Solution/Suspension

A 15–50 mL solution/suspension of the compounds of the invention is made as follows. Zn-protoporphyrin (1.0–10.0 g) is mixed with alcohol (0.0–3.0 mL), sodium benzoate (0.0–50.0 mg), glycerin (0.0–1.5 mL), propylene glycol (0.0–3.0 mL), sweetener (5.0–100 mg), sodium citrate (0.0–250 mg), citric acid (0.0–250 mg), sodium chloride (0.0–250 mg) and purified water (10–40 mL). The compounds may be added in different orders and mixed. Natural or synthetic flavorings such as fruit, maple, bubble gum or others may be used to make the formulation more palatable. Various sweeteners such as fructose, high fructose corn syrup, aspartame, saccharin and others may be used.

9. Preparation of a Formulation for Oral Solution/Suspension

A 15–50 mL solution/suspension of the compounds of the invention is made as follows. Zn-protoporphyrin (1.0–10.0 g) is mixed with alcohol (0.0–3.0 mL), isopropyl myristate (0.0–5.0 g), polyethylene glycol (0.0–5.0 g), and purified water (10–40 mL). The compounds may be added in different orders and mixed. Natural or synthetic flavorings such as fruit, maple, bubble gum or others may be used to make the formulation more palatable. Various sweeteners such as fructose, high fructose corn syrup, aspartame, saccharin and others may be used.

What is claimed is:

1. A method for treating heart failure comprising administering, to a mammal in need of such treatment, a therapeutically effective amount of a compound of the formula II and all its isomeric, chiral, pharmaceutically acceptable salt, prodrug, partially unsaturated, completely salt, prodrug, partially unsaturated, completely unsaturated, forms wherein:

$RA_1$, $RA_2$, $RB_1$, $RB_2$, $RC_1$, $RC_2$, $RD_1$, and $RD_2$ independently selected at each occurrence from:

H, C2–C8 alkenyl, C1–C8 alkyl, C2–C8 alkynyl, formyl, C3–C9 formylalkenyl, C2–C9 formylalkyl, C1–C8 aminoalkyl, C1–C8 hydroxyalkyl, C1–C8 thioalkyl, -carboxy, C2–C8 haloalkyl, C2–C8 carboxyalkyl, (C1–C8)alkoxy-(C1–C8)alkyl, (C1–C8)alkoxy-carbonyl-(C1–C8)alkyl,(C1–C8) alkyl-carbonyl-(C1–C8)alkyl, C2–C12 alkoxycarbonyl, (C1–C8)alkyl-carboxy-(C1–C8) alkyl,(C1–C8)alkyl-carbonyloxy-(C1–C8)alkyl, (C1–C8)alkyl-carbonylamino-(C1–C8)alkyl, (C1–C8)alkyl-carbonylthio-(C1–C8)alkyl,(C1–C8) alkoxy-carbonylamino-(C1–C8)alkyl,aryl(C1–C4) alkyl-oxycarbonylamino-(C1–C8)alkyl,aryl-(C1–C4)alkyl-oxycarbonyloxy-(C1–C8)alkyl, (C1–C8)alkoxy-carbonyloxy-(C1–C8)alkyl, (C1–C8)alkylaminocarbonyl-(C1–C8)alkyl, hydroxy-(C1–C8)alkyloxy-carbonyl-(C1–C8)alkyl, C2–C12 dihydroxyalkyl,aryloxy-(C1–C6)alkyl, aryloxycarbonyl-(C1–C6)alkyl, arylcarbonyloxy-(C1–C8)alkyl, hydroxy substituted carboxy-(C1–C8)alkyl, amino substituted carboxy-(C1–C8) alkyl, thio substituted carboxy-(C1–C8)alkyl, amino acid attached via the amino or carboxyl group, hydroxy acid attached via the hydroxy or carboxyl group, hydroxy substituted amino acid attached via the hydroxy or amino or carboxyl group, pyridinium halide (C2–C8) alkyl, pyridyl-(C2–C8)alkyl, or, $S(=O)_2OR_5$; where,

(1) any of the above amine substituted groups is optionally further substituted with an amine protecting group;

(2) any of the above hydroxy substituted groups is optionally further substituted with a hydroxy protecting group;

(3) any of the above carboxy substituted groups is optionally further substituted with a carboxy protecting group; or (4) any of the pairs of adjacent substituents $RA_1$ and $RA_2$ or $RB_1$ and $RB_2$, $RC_1$ and $RC_2$ or $RD_1$, and $RD_2$ may join together to form a cyclic group selected from the structures:

where the cyclic group is fused to the respective pyrrole ring to which the adjacent pair of substituents is attached;

$RA_3$ and $RA_4$ are independently selected at each occurrence from:

Carboxy-(C2–C6)alkyl, —SO$_2$R$_7$, aryl, aryl-(C1–C6) alkyl, cyano or —C(=O)—NR$_5$—C(=O)—;

$R_5$ is independently selected at each occurrence from:
C1–C6 alkyl, H, aryl or aryl-(C1–C6)alkyl;

$R_6$ is independently selected at each occurrence from:
C1–C6 alkyl, H, aryl, aryl-(C1–C6)alkyl or any R$_6$ group may be absent when an M group is coordinated to its corresponding pyrrole ring nitrogen;

$R_7$ is independently selected at each occurrence from:
C6–C10 aryl or C1–C8 alkyl;

M is independently selected at each occurrence from:
Zn, Fe, Mn, Mg, Sn, Ni, Cu, Ca, Ba, Cd, Sr, Ga or Pt;

X is independently selected at each occurrence from:
—S—, —NR$_5$— or —O—;

n is independently selected at each occurrence from 1, 2, 3 or 4;

aryl is independently selected at each occurrence from:
Phenyl, naphthenyl or biphenyl; where said phenyl, napthenyl or biphenyl groups are independently:
(1) unsubstituted; or
(2) substituted with 1–3 substituents independently selected from: —Fl, —Cl, —Br, —I, C1–C4 alkyl or C1–C4 alkoxy; and

- - - is independently saturated or unsaturated at each occurrence as long as the resulting compound is stable;

to allow an increase in cardiac contractility.

2. The method for treating heart failure as recited in claim 1 further comprising: maintaining in the mammal, for a sufficient period of time, a therapeutically effective amount of the compound of the formula II to allow an increase in cardiac contractility.

3. The method for treating heart failure as recited in claim 2 further comprising: ceasing administration of the compound of the formula II upon resolution of heart failure.

4. The method for treating heart failure as recited in claim 1, where the compound of the formula II accumulates in cardiac myocytes.

5. The method for treating heart failure as recited in claim 1, further comprising: readministering to the mammal a therapeutically effective amount of the compound of the formula II.

6. The method for treating heart failure as recited in claim 2, where the therapeutically effective amount of the compound of the formula II is maintained using either one or a combination of dosage forms such as controlled, sustained, timed, delayed or extended release, or long-acting or short-acting dosage forms.

7. The method for treating heart failure as recited in claim 2, where the therapeutically effective amount of the compound of the formula II is maintained using either one or a combination of dosage regimens such as repeated administration of short-acting dosage form, continuous or semicontinuous infusion of injectable dosage form, repeated injection or injectable dosage form, repeated administration of extended, timed, sustained, delayed or controlled release dosage forms.

8. The method for treating heart failure as recited in claim 1, wherein:

$RA_1$, $RA_2$, $RB_1$, $RB_2$, $RC_1$, $RC_2$, $RD_1$, and $RD_2$ are independently selected at each occurrence from:
H, C2–C8 alkenyl, C1–C8 alkyl, formyl, C3–C9 formylalkenyl, C2–C9 formylalkyl, C1–C8 hydroxyalkyl, C1–C8 thioalkyl, -carboxy, C2–C8 haloalkyl, C2–C8 carboxyalkyl, (C1–C8)alkoxy-(C1–C8)alkyl,(C1–C8)alkoxy-carbonyl-(C1–C8) alkyl, (C1–C8)alkyl-carbonyl-(C1–C8)alkyl, C2–C12 alkoxycarbonyl,(C1–C8)alkyl-carboxy-(C1–C8)alkyl,(C1–C8)alkyl-carbonyloxy-(C1–C8) alkyl,(C1–C8)alkyl-carbonylamino-(C1–C8)alkyl, (C1–C8)alkyl-carbonylthio-(C1–C8) alkyl, aryl (C1–C4)alkyl-oxycarbonyloxy-(C1–C8)alkyl, (C1–C8)alkoxy-carbonyloxy-(C1–C8)alkyl, hydroxy-(C1–C8)alkyloxy-carbonyl-(C1–C8)alkyl, C2–C12 dihydroxyalkyl, aryloxy-(C1–C6)alkyl, aryloxycarbonyl-(C1–C6)alkyl, arylcarbonyloxy-(C1–C8)alkyl,hydroxy substituted carboxy-(C1–C8) alkyl, amino substituted carboxy-(C1–C8)alkyl, thio substituted carboxy-(C1–C8)alkyl, amino acid attached via the amino or carboxyl group, hydroxy acid attached via the hydroxyl or carboxyl group, hydroxy substituted amino acid attached via the hydroxy or amino or carboxyl group, pyridinium halide (C2–C8) alkyl, pyridyl-(C2–C8)alkyl, or, S(=O)$_2$OR$_5$; where, (1) any of the above amine substituted groups is optionally further substituted with an amine protecting group;
(2) any of the above hydroxy substituted groups is optionally further substituted with a hydroxy protecting group;
(3) any of the above carboxy substituted groups is optionally further substituted with a carboxy protecting group; or
(4) any of the pairs of adjacent substituents $RA_1$ and $RA_2$ or $RB_1$ and $RB_2$, $RC_1$ and $RC_2$ or $RD_1$, and $RD_2$ may join together to form a cyclic group selected from the structures:

where the cyclic group is fused to the respective pyrrole ring to which the adjacent pair of substituents is attached;

M is independently selected at each occurrence from:
Zn, Fe, Mn, Mg, Sn, Ni, Cu, Ca, Ba or Cd; the method further comprising:
maintaining in the mammal, for a sufficient period of time, a therapeutically effective amount of the compound of the formula II to allow an increase in cardiac contractility.

9. The method for treating heart failure as recited in claim 8, wherein:

$RA_1$, $RA_2$, $RB_1$, $RB_2$, $RC_1$, $RC_2$, $RD_1$, and $RD_2$ independently selected at each occurrence from:

H, C2–C8 alkenyl, C1–C8 alkyl, formyl, C2–C8 haloalkyl, C1–C8 thioalkyl, C3–C9 formylalkenyl, C2–C9 formylalkyl, C1–C8 hydroxyalkyl, (C1–C8)alkoxy-(C1–C8)alkyl, (C1–C8)alkoxy-carbonyl-(C1–C8)alkyl, (C1–C8)alkyl-carboxy-(C1–C8)alkyl, (C1–C8)alkyl-carbonyloxy-(C1–C8)alkyl, (C1–C4)alkoxy-carbonyloxy-(C1–C8)alkyl, (C1–C8)alkoxy-carbonyloxy-(C1–C8)alkyl, C2–C12 dihydroxycarbonyl, aryloxy-(C1–C6)alkyl, aryloxycarbonyl-(C1–C6)alkyl, arylcarbonyloxy-(C1–C8)alkyl, hydroxy substituted carboxy-(C1–C8)alkyl, amino acid attached via the amino or carboxyl group, hydroxy acid attached via the hydroxy or carboxyl group, pyridinium halide (C2–C8) alkyl, pyridyl-(C2–C8)alkyl, or, $S(=O)_2OR_5$; where, (1) any of the above amine substituted groups is optionally further substituted with an amine protecting group;

(2) any of the above hydroxy substituted groups is optionally further substituted with a hydroxy protecting group;

(3) any of the above carboxy substituted groups is optionally further substituted with a carboxy protecting group; or (4) any of the pairs of adjacent substituents $RA_1$ and $RA_2$ or $RB_1$ and $RB_2$, $RC_1$ and $RC_2$ or $RD_1$, and $RD_2$ may join together to form a cyclic group selected from the structures:

where the cyclic group is fused to the respective pyrrole ring to which the adjacent pair of substituents is attached; and (5) the amino acid is independently selected at each occurrence from: Ala, Arg, Asn, Asp, Cys, DBA, GABA, Gln, Glu, Gly, HB, Ile, Leu, Lys, Met, Phe, Pro, Ser, Thr, Trp, Tyr and Val; and M is independently selected at each occurrence from: Zn, Fe, Mn, Mg, Sn, Ca or Ba.

10. The method for treating heart failure as recited in claim 8, wherein:

$RA_1$, $RC_1$, and $RD_2$ are independently selected at each occurrence from H or —$CH_3$;

$RA_2$ and $RB_2$, are independently selected at each occurrence from:
—$CH_2(OR_5)CH_3$—, —$CH_2CH_3$, —CH=$CH_2$—, —$CH_2$—$CO_2R_5$, —C(=O)H, —$CH_2CH_2CH_3$, H, =CH—C(=O)H, —CH(SH)$CH_3$, —CH(Br)$CH_3$, —CH($OR_5$)$CH_2OR_5$, pyridinium halide (C2–C8) alkyl, pyridyl-(C2–C8)alkyl, or —$SO_3R_5$;

$RB_1$ is formyl or H;

$RC_2$ and $RD_1$ are independently selected at each occurrence from:
—$CH_2CH_2CO_2R_5$, —$CH_2CO_2R_5$, —$CH_2R_5$, —$CH_2CH_2CH_3$ or H; and M is independently selected at each occurrence from: Zn, Fe, Mn, Mg or Sn.

11. The method for treating heart failure as recited in claim 10, wherein the compound of the formula II were selected from:

deuteroporphyrin IX disulfonate, deuteroporphyrin IX bisglycol, coproporphyrin I, hematoporphyrin IX dimethyl ester, hematoporphyrin IX, deuteroporphyrin IX dimethyl ester, N-phenylproto-porphyrin IX, Ferro-protoporphyrin IX, Zinc-protoporphyrin IX, Manganese-protoporphyrin IX or Tin-protoporphyrin IX.

* * * * *